US007847087B2

(12) United States Patent
Huong et al.

(10) Patent No.: US 7,847,087 B2
(45) Date of Patent: Dec. 7, 2010

(54) METHODS AND PRIMERS FOR EVALUATING HIV-1 MUTATIONS

(75) Inventors: Tzong-Jyh Huong, Norcross, GA (US); Robert M. Lloyd, Jr., Suwanee, GA (US); Arejas Uzgiris, Roslindale, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 933 days.

(21) Appl. No.: 10/469,313

(22) PCT Filed: Mar. 5, 2002

(86) PCT No.: PCT/US02/06632

§ 371 (c)(1), (2), (4) Date: May 21, 2004

(87) PCT Pub. No.: WO02/070731

PCT Pub. Date: Sep. 12, 2002

(65) Prior Publication Data

US 2005/0084854 A1 Apr. 21, 2005

Related U.S. Application Data

(60) Provisional application No. 60/273,683, filed on Mar. 5, 2001.

(51) Int. Cl.
*C07H 21/04* (2006.01)
*C12P 19/34* (2006.01)
(52) U.S. Cl. .................................. 536/24.33; 435/91.2
(58) Field of Classification Search ........................ None
See application file for complete search history.

(56) References Cited

U.S. PATENT DOCUMENTS

| 5,837,464 A | | 11/1998 | Capon et al. |
| 5,962,665 A | * | 10/1999 | Kroeger et al. ............. 536/23.1 |
| 5,985,544 A | | 11/1999 | Kasper et al. |
| 6,194,142 B1 | | 2/2001 | Moncany et al. |

FOREIGN PATENT DOCUMENTS

| JP | 08-242898 | 9/1996 |
| JP | 10-117780 | 5/1998 |
| JP | 2004-500840 | 1/2004 |
| WO | WO 92/16181 | 10/1992 |
| WO | WO 99/67428 | 12/1999 |
| WO | WO 01/81624 A1 | 11/2001 |

OTHER PUBLICATIONS

Buck et al. Design strategies and performance of custom DNA sequencing primers. BioTechniques 27:528-536 (Sep. 1999).*
GenBank entry GI:2801501 (6 pages).*
Triques et al. Efficiencies of four versions of the AMPLICOR HIV-1 Monitor test for quantification of different subtypes of human immunodeficiency virus type 1. J Clin Microbiol. Jan. 1999;37(1):110-6.*
GenBank® GI: 4416536 [online], Mar. 15, 1999, [retrieved on Apr. 23, 2007], retrieved from the Internet: <URL: www.ncbi.nlm.nih.gov/entrez/viewer.fcgi?db=nucleotide&val=4416536>.*
Davies et al., Molecular Genotyping of HIV-1 in 61 Patients with AIDS From Lome, Togo, Journal of Medical Virology, 1999, pp. 25-30, vol. 57.
Durant et al., Drug-resistance genotyping in HIV-1 therapy: the VIRADAPT randomised controlled trial, The Lancet, Jun. 26, 1999, pp. 2195-2199, vol. 353, XP-002169511.
Sarkar et al., Dideoxy Fingerprinting (ddF): A Rapid and Efficient Screen for the Presence of Mutations, Genomics, Jan. 21, 1992, pp. 441-443, vol. 13.
Schinaze et al., Mutations in retroviral genes associated with drug resistance, International Antiviral News, 1947, pp. 129-142, vol. 5, No. 8.
Davies et al., Molecular geneotyping of HIV-1 in 61 patients with AIDS from Lome, Togo, J. of Med. Virology, 57: 25-30 (1999).
Vergne et al., Genetic Diversity of Protease and Reverse Transcriptase Sequences in Non-subtype-B Human Immunodeficiency Virus Type 1 Strains: Evidence of Many Minor Drug Resistance Mutations in Treatment-Naive Patients, J. of Clinical Microbiology, 38(11): 3919-3925, (2000).
Niubo et al., Recovery and analysis of human immunodeficiency virus type 1 (HIV) RNA sequences from plasma samples with low HIV RNA levels, J. Clin. Micro., vol. 38: 309-312 (2000).
Database Nuceotide, NCBI, Database accession No. NC-001802, (2005).
Donehower, Lawrence A., et al., "The use of primers from highly conserved *pol* regions to identify uncharacterized retroviruses by the polymerase chain reaction," 28(1) *Journal of Virological Methods* 33-46 (Apr. 1990).
Tanuri, Amilcar, et al., "HIV-1 Subtypes Among Blood Donors from Rio de Janeiro, Brazil," 20 *Journal of Acquired Immune Deficiency Syndromes and Human Retrovirology* 60-66 (1999).

* cited by examiner

*Primary Examiner*—Samuel Woolwine

(57) ABSTRACT

Primer sequences and a method of using such sequences for the genotyping of HIV-1-containing samples, particularly those which have failed genotyping analysis are provided using primer sequences designed for analysis of Group B subtype of the Group M type virus. For example, a combination of primers, including at least one species of forward primer and at least one species of reverse primer where the forward primer(s) can be represented by the degenerate sequence: RARRARGGGCTGYTGGARATGTS (Seq. ID No. 9) and the reverse primer(s) can be represented by the degenerate sequence: BCHTYACYTTRATCCCSGVRT-ARATYTGACT (Seq. ID No.: 10) or BCHTYACYT-TRATCCCSGVRTARATYTGAC (Seq. ID No. 12) are suitably employed. The selected primers, one or more from each group, can be used as reverse transcription, amplification and sequencing primers and are suitably packaged in a genotyping kit. Such a kit may include reagents in addition to the primers, such as an RNase inhibitor, a reverse transcriptase, a polymerase, and/or dNTP and ddNTP feedstocks.

26 Claims, No Drawings

SEQUENCE LISTING

<160> NUMBER OF SEQ ID NOS: 19

<210> SEQ ID NO 1
<211> LENGTH: 24
<212> TYPE: DNA
<213> ORGANISM: human immunodeficiency virus

<400> SEQUENCE: 1
ggaaaaaggg ctgttggaaa tgyg                24

<210> SEQ ID NO 2
<211> LENGTH: 25

```
<212> TYPE: DNA
<213> ORGANISM: human immunodeficiency virus

<400> SEQUENCE: 2
grarrarggg ctgttggaaa tgtgg                                        25

<210> SEQ ID NO 3
<211> LENGTH: 24
<212> TYPE: DNA
<213> ORGANISM: human immunodeficiency virus

<400> SEQUENCE: 3
grarrarggg ctgttggaaa tgtg                                         24

<210> SEQ ID NO 4
<211> LENGTH: 31
<212> TYPE: DNA
<213> ORGANISM: human immunodeficiency virus

<400> SEQUENCE: 4
agtcagattt acccagggat taaagtaagg v                                 31

<210> SEQ ID NO 5
<211> LENGTH: 31
<212> TYPE: DNA
<213> ORGANISM: human immunodeficiency virus

<400> SEQUENCE: 5
agtcagattt acccagggat taaggtaagg v                                 31

<210> SEQ ID NO 6
<211> LENGTH: 31
<212> TYPE: DNA
<213> ORGANISM: human immunodeficiency virus

<400> SEQUENCE: 6
agtcagattt acccagggat caaagtaagg v                                 31

<210> SEQ ID NO 7
<211> LENGTH: 30
<212> TYPE: DNA
<213> ORGANISM: human immunodeficiency virus

<400> SEQUENCE: 7
gycagattta cccagggatt aaagtaaggc                                   30

<210> SEQ ID NO 8
<211> LENGTH: 31
<212> TYPE: DNA
<213> ORGANISM: human immunodeficiency virus

<400> SEQUENCE: 8
agycagattt acccagggat taaagtaagg c                                 31

<210> SEQ ID NO 9
<211> LENGTH: 23
<212> TYPE: DNA
<213> ORGANISM: human immunodeficiency virus

<400> SEQUENCE: 9
rarrargggc tgytggarat gts                                          23

<210> SEQ ID NO 10
```

<210> SEQ ID NO 10
<211> LENGTH: 31
<212> TYPE: DNA
<213> ORGANISM: human immunodeficiency virus

<400> SEQUENCE: 10
agtcaratyt aybcwgggat yaargtradg v                              31

<210> SEQ ID NO 11
<211> LENGTH: 24
<212> TYPE: DNA
<213> ORGANISM: human immunodeficiency virus

<400> SEQUENCE: 11
ggaaaaaggg ctgttggaaa tgtc                                      24

<210> SEQ ID NO 12
<211> LENGTH: 30
<212> TYPE: DNA
<213> ORGANISM: human immunodeficiency virus

<400> SEQUENCE: 12
gtcaratyta ybcwgggaty aargtradgv                                30

<210> SEQ ID NO 13
<211> LENGTH: 30
<212> TYPE: DNA
<213> ORGANISM: human immunodeficiency virus

<400> SEQUENCE: 13
gtcagattta cccagggatt aaagtaaggc                                30

<210> SEQ ID NO 14
<211> LENGTH: 30
<212> TYPE: DNA
<213> ORGANISM: human immunodeficiency virus

<400> SEQUENCE: 14
gccagattta cccagggatt aaagtaaggc                                30

<210> SEQ ID NO 15
<211> LENGTH: 23
<212> TYPE: DNA
<213> ORGANISM: human immunodeficiency virus

<400> SEQUENCE: 15
gaaaaagggc tgttggaaat gtg                                       23

<210> SEQ ID NO 16
<211> LENGTH: 23
<212> TYPE: DNA
<213> ORGANISM: human immunodeficiency virus

<400> SEQUENCE: 16
gaaaaagggc tgttggaaat gcg                                       23

<210> SEQ ID NO 17
<211> LENGTH: 25
<212> TYPE: DNA
<213> ORGANISM: human immunodeficiency virus

<400> SEQUENCE: 17
ggaaaaaggg ctgttggaaa tgtgg                                     25

```
<210> SEQ ID NO 18
<211> LENGTH: 24
<212> TYPE: DNA
<213> ORGANISM: human immunodeficiency virus

<400> SEQUENCE: 18
ggaaaaaggg ctgttggaaa tgtg                                        24

<210> SEQ ID NO 19
<211> LENGTH: 25
<212> TYPE: DNA
<213> ORGANISM: human immunodeficiency virus

<400> SEQUENCE: 19
ggaaaaaggg ctgttggaaa tgtcg                                       25
```

METHODS AND PRIMERS FOR EVALUATING HIV-1 MUTATIONS

This application is a 371 national phase of PCT/US02/06632, filed Mar. 5, 2002, and claims the benefit of U.S. Provisional Application No. 60/273,683, filed Mar. 5, 2001.

BACKGROUND OF THE INVENTION

The present application relates to methods and primers for evaluating mutations in human immunodeficiency virus (HIV-1).

Human immunodeficiency virus is the primary causative agent of Acquired Immune Deficiency Syndrome (AIDS), or AIDS-related complex (ARC). AIDS is an infectious disease characterized by generalized immune suppression, multiple opportunistic infections, and neurological disease. Although HIV is regarded to be the primary causative agent of AIDS, multiple co-infecting clinical viral and bacterial pathogens are responsible for the cluster of clinical syndromes seen in AIDS patients.

The clinical course of HIV infection is remarkable for its great variability. The clinical effects include increased susceptibility to opportunistic infections and rare cancers, such as Kaposi's sarcoma, neurological dysfunctions, leading to AIDS related dementias, and generalized immune dysfunctions.

The HIV-1 virus is a member of the lentivirus group of the retroviruses. Like all other retroviruses, it has an RNA genome which is replicated via the viral reverse transcriptase, into a DNA provirus which becomes integrated into the host cell genome.

Various drugs are presently available to treat HIV. They fall into three different classes—nucleoside reverse transcriptase inhibitors, or NRTI's such as zidovudine, didanosine, zalcitabine, lamivudine, stavudine, abacavir, tenofovir, foscarnet; non-nucleoside reverse transcriptase inhibitors or NNRTI's such as nevirapine, delavirdine, efavirenz; and protease inhibitors or PI's such as saquinavir, indinavir, ritonavir, nelfinavir, amprenavir, and lopinavir with ritonavir. Although some of these drugs may have similar modes of actions, resistance to one does not necessarily confer resistance to another.

Each of the presently available anti-retroviral compounds used to treat AIDS suffers from some disadvantages, including transient CD4 cell count effects, incomplete inhibition of viral replication, toxicity at prescribing doses, and emergence of resistant forms of the virus. As a result, combination therapies are being used to treat patients. Several in vitro studies have suggested that the combination of two or more anti-HIV compounds will more effectively inhibit HIV replication than each drug alone. Over the last several years, the standard of patient care has evolved such that HIV patients are routinely treated with triple drug combination therapy.

Combination therapy has significantly decreased HIV associated morbidity and mortality. However, a large number of patients are not able to achieve or maintain complete viral suppression even with combination therapy. Drug resistance is the consequence of this incomplete viral suppression. The very high mutagenicity rate of HIV virus (due to the error-prone nature of the viral reverse transcriptase) and the genetic variability of the virus have led to many HIV variants with decreased drug susceptibility.

HIV-1 replication depends on a virally encoded enzyme, reverse transcriptase (RT) that copies the single-stranded viral RNA genome into a double-stranded DNA/RNA hybrid. The HIV-1 RT enzyme lacks a 3' exonuclease activity which normally helps the "proof-reading" function of a polymerase enzyme to repair errors. HIV-1 has a 9200-base genome and, on average, RT makes at least one error during every transcription of 10,000 bases copied. Therefore, each progeny virus produced may be slightly different from its predecessor. The inaccuracy of RT results in an estimated in vivo forward mutation rate of $3 \times 10^{-5}$ per base incorporated. Mansky L M. Virology. 1996; 222:391-400.

Many mutations introduced into the HIV-1 genome will compromise the infectivity of the virus; while some are compatible with virus infectivity. The frequency with which genetic variants of HIV-1 are detected in patients is a function of each variant's replicative vigor (fitness) and the nature of the selective pressures that may be acting on the population within the infected patient, Volberding P A, et al., Antiretroviral therapy for HIV infection: promises and problems. JAMA. 1998; 279:1343-4. Selective pressures existing in HIV-1 infected persons include anti-HIV-1 immune responses, the availability of host cells that are susceptible to virus infection in different tissues, and the use of antiretroviral drug treatments.

The mutagenicity of the virus represents a significant barrier to treatment of the disease. Moreover, the mutagenicity of the virus makes testing for genetic changes in the virus very difficult. Testing for changes in DNA sequence can proceed via complete sequencing of a target nucleic acid molecule, although many persons in the art believe that such testing is too expensive to ever be routine.

Attention has been increasingly focused on failure to achieve or maintain viral suppression. Several factors may contribute to drug failure, including poor patient adherence to treatment regimen, drug potency, pharmacokinetic issues (related to antiretroviral drug absorption, metabolism, excretion, and drug-drug interactions) and drug resistance Vella S, et al. Aids. 1998; 12:S147-8.b. Although multiple combinations of antiretroviral drugs may suppress HIV-1 below the level of HIV-1 RNA detection, this does not mean that the virus is not replicating in "sanctuary" compartments. A therapy regimen may decrease HIV-1 RNA to below detectable levels, but within months the HIV-1 viral load may increase again. If HIV-1 is replicating, resistance to therapy can develop.

Because HIV-1 replication occurs rapidly, large numbers of virus variants, including those that display diminished sensitivity to antiretroviral drugs, are generated. Mutations that confer resistance to antiretroviral drugs can be present in HIV-1 infected persons before antiretroviral therapy is initiated due to transmission from an individual having had prior therapy or due to spontaneously arising mutations. Once drug therapy is initiated, the pre-existing population of drug-resistant viruses can rapidly predominate because of a selective advantage. For drugs such as lamivudine or nevirapine (and other NNRTIs), a single nucleotide change in the HIV-1 RT gene can confer 100- to 1,000-fold reductions in drug susceptibility (Schinazi RF, et al Int Antiviral News. 1997; 5:129-42). In vivo antiretroviral activity of these drugs, when used alone, is largely lost within 4 weeks of starting therapy due to the rapid outgrowth of drug-resistant variants, Richman D D, et al. Nevirapine resistance mutations of human immunodeficiency virus type 1 selected during therapy. J Virol. 1994; 68:1660-6. Some mutations selected by antiretroviral drugs directly affect viral enzymes and cause resistance via decreased drug binding, whereas others have indirect effects. Condra J H, et al. J Virol. 1996; 70:8270-6, and Harrigan P R, et al. J Virol. 1996; 70:5930-4. Treatment with different antiretroviral drugs may select for HIV-1 variants that harbor the same, or related, mutations. Treatments may even select for the outgrowth of HIV-1 variants that are resistant to drugs to which the patient has not yet been exposed (cross-resistance).

Mutations can be detected by a technique called "single stranded conformational polymorphism" (SSCP) described by Orita et al., Genomics 5: 874-879 (1989), or by a modification thereof referred to as dideoxy-fingerprinting ("ddF") described by Sarkar et al, Genomics 13: 441-443 (1992). SSCP and ddF both evaluate the pattern of bands created when DNA fragments are electrophoretically separated on a non-denaturing electrophoresis gel. This pattern depends on a combination of the size of the fragments and the three-dimensional conformation of the undenatured fragments. Thus, the pattern can not be used for sequencing, because the theoretical spacing of the fragment bands is not equal.

Others have attempted to determine the genetic status of the virus by probe-based analyses, in which the presence or absence of a specific viral mutation is determined by whether or not an inquiry probe hybridizes to the viral nucleic acid under specific hybridization conditions. For example, Stuyver et al. (PCT International Publication No. WO 99/67428) describe the use of nucleic acid probe panels in a reverse hybridization assay, and Gingeras et al. describe the use of probes to detect pairs of mutations (PCT International Publication No. WO 92/16180). Such assays may suffer from several deficiencies, including being unable to detect new viral mutants, and may not be sensitive enough to cope with the complexity of many mutations within a region.

Other methods include the use of resistance test vectors to culture host cells with virus derived from a patient. The vector may include an indicator gene, such that when a test amount of an anti-HIV drug is added to the cell culture, in an attempt to measure the resistance of the cloned virus to the drug in the cell culture system. (Parkin et al, U.S. Pat. No. 5,837,464).

By far, the most direct information about the genetic composition of the virus in a patient is to directly determine the sequence of the virus (genotyping). The positive clinical benefit of genotyping has been demonstrated in controlled retrospective and prospective intervention based studies such as the Genotypic Antiretroviral Resistance Testing (GART) (Baxter J D, et al. A randomized study of antiretroviral management based on plasma genotypic antiretroviral resistance testing in patients failing therapy. AIDS; 2000; 14; F83-F93 and VIRADAPT studies, Durant J, et al. Drug-resistance genotyping in HIV-1 therapy: the VIRADAPT randomised controlled trial, Lancet. 1999; 353:2195-9 and Lancet 1999 Sep. 25; 354(9184):1128. The greater reduction in viral load when the identification of mutations associated with resistance to specific antiretroviral drugs is used as an adjunct to standard of care in treated patients has demonstrated the clinical benefit of the adjunctive use of genotyping to guide therapeutic decisions.

One of the difficulties of genotyping is the inherent variability and heterogeneity of the virus. Viruses have been found to be serologically different on the basis of reactivity of the host immune system to the virus, and on the basis of ELISAs, antibody dependent cellular cytotoxicity assays (ADCC's), and CD4 inactivation procedures. The extensive serologic heterogeneity of the virus is also mirrored in the genetic sequences of the virus. As a result, the HIV-1 virus has been categorized into two genetic groups, based on phylogenetic reconstruction using the viral DNA sequences. Group O (outlier) represents a minority of the HIV-1, and is thought to originate in West Africa, perhaps in Cameroon.

The vast majority of HIV-1 sequences that are associated with clinical AIDS are of the Group M (major) type. Within the M group, there are various subtypes (also referred to as clades), having different geographic distributions, as shown below.

| HIV-1 Group M Subtype | Predominant geographical location |
|---|---|
| A (including A1 and A2) | Central Africa |
| B | Europe, North and South America, Australia, and Asia |
| C | East and South Africa, India |
| D | Central Africa |
| E | Southeast Asia (Thailand) |
| F (including F1 and F2) | South America (Brazil) and Eastern Europe (Romania) |
| G | Central Africa, Russia, and Portugal |
| H | Central Africa and Taiwan |
| I | Cyprus |
| J | Central Africa and Europe |
| K | |
| N | |
| O | |

Each subtype differs from the others in amino acid composition by at least 20% in the viral envelope region, and at least 15% in the viral gag region. Within each subtype, the differences in env can be up to 10%, while the differences in gag can be Up to 8%. The viral reverse transcriptase and protease genes, the sites known to be associated with drug resistance, are found on the viral pol transcript. It is estimated that there is only a 75% similarity in amino acids between subtypes for HIV-1 pol. The variability at the nucleic acid sequence level is even greater.

Retroviruses have propensity to recombine with related retroviruses. If one cell is infected with multiple viruses, recombination events may occur, leading to recombinant subtypes that may then infect other individuals. In addition to the various subtypes known, circulating recombinant subtypes have been observed, such as A/E (Central Africa), A/G (West and Central Africa), A/B (Kalingrad), A/G/H/K (Cyprus/ Greece) as well as D/F, and B/D recombinants.

To date, the majority of clinical research in North America and Western Europe has been directed to the Group M subtype B, due to its relative prevalence over the other Group M subtypes. However, as the AIDS epidemic has spread, non-B subtypes are appearing with increasing frequency in North America and Europe. In some instances, for example, an initial infected person with a non-B infection may serve as the infection focal point for a local group, such that in some North American centers (which remain predominantly B subtype), there can be entire localized population groups infected with non-B subtypes. For example, Group O and Subtype G of Group M have recently been found in AIDS patients arriving in the United States from Africa.

SUMMARY OF THE INVENTION

The present invention provides primer sequences, and a method of using such sequences for the genotyping of HIV-1-containing samples, particularly those which have failed genotyping analysis using primer sequences designed for analysis of Group B subtype of the Group M type virus. Thus, a first aspect of the present invention is a combination of primers, including at least one species of forward primer and at least one species of reverse primer. The forward primer(s) can be represented by the degenerate sequence:

RARRARGGGCTGYTGGARATGTS        (Seq ID No. 9)

optionally with an additional G at either or both ends, where the non-standard letters (those others than A, C, G and T) reflect choices of bases in accordance with conventional nomenclature as outlined below. There are a total of 128 possible sequences represented by this sequence. Variations of these sequences may also be employed. For example, Seq. ID Nos. 11, 15 and 16 show primers where one G is added. Similarly, the reverse primer(s) can be represented by the degenerate sequence:

AGTCARATYTAYBCWGGGATYAARGTRADGV   (Seq. ID No.: 10)
    or
    GTCARATYTAYBCWGGGATYAARGTRADGV    (Seq. ID No. 12)

In the former case, there are a total of 3456 possible primer species within this definition. In the latter case, the degenerate sequence also represents 3456 possible sequences, differing only in the initial A. The selected primers, one or more from each group, can be used as reverse transcription, amplification and sequencing primers.

The primers are suitably packaged in a genotyping kit. Such a kit may include reagents in addition to the primers, such as an RNase inhibitor, a reverse transcriptase, a polymerase, and/or dNTP and ddNTP feedstocks.

The primers are suitably employed in the method of the invention. In accordance with this method, a sample suspected of containing a non-B Group M HIV-1 virus or a Group O HIV-1 virus is treated to recover viral RNA. The recovered viral RNA is reverse transcribed to DNA, which is sequenced using the primers of the invention. The resulting sequence information is used to establish the genotype of the tested virus, i.e., to determine to which subtype the virus in the sample belongs. The method of the invention may be practiced in parallel with genotyping procedures that are designed to evaluate B-subtype virus. Alternatively, the method of the invention is practiced on samples that have previously been the subject of a failed genotyping attempt using genotyping procedures that are designed to evaluate B-subtype virus.

DETAILED DESCRIPTION OF THE INVENTION

While the terminology used in this application is standard within the art, the following definitions of certain terms are provided to assure clarity.

The term "allele" as used herein means a specific version of a nucleotide sequence at a polymorphic genetic locus.

The term "polymorphic site" as used herein means a given nucleotide location in a genetic locus which is variable within a population.

The term "gene" or "genetic locus" as used herein means a specific nucleotide sequence within a given genome.

The term "location" or "position" of a nucleotide in a genetic locus means the number assigned to the nucleotide in the gene, generally taken from the cDNA sequence of the genomic sequence of a gene.

The nucleotides adenosine, cytosine, guanine and thymine are represented by their one-letter codes A, C, G, and T respectively. In representations of degenerate primers, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide. In the specification and claims of this application, a degenerate primer refers to any or all of the combinations of base choices and to either DNA or the corresponding RNA sequence (i.e., with T replaced by U). Thus, a degenerate primer may represent a single species, or a mixture of two species which fall within the choices, or a mixture of three choices which fall with the choices, and so on up to a mixture containing all the possible combinations.

The term "oligonucleotide primer" as used herein defines a molecule comprised of more than three deoxyribonucleotides or ribonucleotides. Its exact length will depend on many factors relating to the ultimate function and use of the oligonucleotide primer, including temperature, source of the primer and use of the method. The oligonucleotide primer is capable of acting as an initiation point for synthesis when placed under conditions which induce synthesis of a primer extension product complementary to a nucleic acid strand. The conditions can include the presence of nucleotides and an inducing agent such as a DNA polymerase at a suitable temperature and pH. In the preferred embodiment, the primer is a SS oligodeoxyribonucleotide of sufficient length to prime the synthesis of an extension product from a specific sequence in the presence of an inducing agent. In the preferred embodiment, the oligonucleotide primers are at least 18 nucleotides long. Sensitivity and specificity of the oligonucleotide primers are determined by the primer length and uniqueness of sequence within a given sample of template nucleic acid. Primers which are too short, for example, may show non-specific binding to a wide variety of sequences.

A first aspect of the present invention is a primer combination comprising, in a single solution, at least one forward HIV-1 primer selected from among primers comprising a sequence as represented by the degenerate sequence of Seq ID Nos. 9, for example Seq. ID. Nos. 11, 15 or 16, and preferably from among primers with exactly these sequences, at least one reverse HIV-1 primer selected from among primers comprising a sequence as represented by the degenerate sequences of Seq. ID Nos. 10 or 12, for example Seq. ID. Nos. 13 or 14, and preferably from among primers with exactly these sequences. Where the primers are to be used as sequencing primers, the forward primers or the reverse primers are labeled with a detectable label. For most common sequencing instruments, a fluorescent label is desirable, although other labels types including colored, chromogenic, fluorogenic (including chemiluminescent) and radiolabels could also be employed. The primer combination may include other reagents appropriate for reverse transcription, amplification or sequencing, and may, of course, include HIV-1 genetic material for analysis.

Specific forward primers for use in the primer combinations of the invention are:

GGAAAAAGGGCTGTTGGAAATGYG        (Seq. ID No. 1)
    GRARRARGGGCTGTTGGAAATGTGG       (Seq. ID No. 2)
    GRARRARGGGCTGTTGGAAATGTG        (Seq. ID No. 3)

including without limitation the following non-degenerate primer sequences:

```
GGAAAAAGGGCTGTTGGAAATGTGG     (Seq. ID No. 17)

GGAAAAAGGGCTGTTGGAAATGTG      (Seq. ID No. 18)

GGAAAAAGGGCTGTTGGAAATGTCG     (Seq. ID No. 19)

GGAAAAAGGGCTGTTGGAAATGTC      (Seq. ID No. 11)

GAAAAAGGGCTGTTGGAAATGTG       (Seq. ID No. 15)

GAAAAAGGGCTGTTGGAAATGCG.      (Seq. ID No. 16)
```

Specific reverse primers for use in the primer combinations of the invention are:

```
AGTCAGATTTACCCAGGGATTAAAGTAAGGV   (Seq. ID No. 4)
AGTCAGATTTACCCAGGGATTAAGGTAAGGV   (Seq. ID No. 5)
AGTCAGATTTACCCAGGGATCAAAGTAAGGV   (Seq. ID No. 6)
GYCAGATTTACCCAGGGATTAAAGTAAGGC    (Seq. ID No. 7)
AGYCAGATTTACCCAGGGATTAAAGTAAGGC   (Seq. ID No. 8)
``` including without limitation the following non-degenerate primer sequences:

```
GTCAGATTTACCCAGGGATTAAAGTAAGGC   (Seq. ID No.: 13)

GCCAGATTTACCCAGGGATTAAAGTAAGGC   (Seq. ID No.: 14)
```

The primer combinations described above can be used in a method in accordance with the invention for a sample suspected of containing a non-B Group M HIV-1 virus or a Group O HIV-1 virus to assess the subtype and genotype of the virus. The method comprises the steps of treating the sample to recover viral RNA; reverse transcribing the recovered viral RNA; sequencing the reverse transcription product; and using the results of the sequencing step to establish the genotype of the tested virus. In this method, either or both of the reverse transcription step and the sequencing step are performed using a primer combination as described above. The method of the invention can include the step of performing a parallel genotyping procedure that is designed to evaluate B-subtype virus. Alternatively, the method can be utilized with a sample that has previously been the subject of a failed genotyping attempt using genotyping procedures that are designed to evaluate B-subtype virus. This alternative method provides the advantage of not performing needless testing on a sample that proves to be the presently more common B-subtype.

Example 1

Degenerate mixtures of forward primers of the sequence

```
GGAAAAAGGGCTGTTGGAAATGYG    (Seq. ID No. 1)
``` and reverse primers of the sequence

```
GYCAGATTTACCCAGGGATTAAAGTAAGGC   (Seq. ID No. 7)
``` were used to salvage non-B subtypes in samples that could not be genotyped using other primers. The TRUGENE HIV-1 genotyping kit (Visible Genetics Inc., Toronto, Canada) was used to determine the genotype of certain non-B subtypes of HIV-1 virus. RNA was extracted from patient plasma samples according to the package instructions in a TRUPREP Extraction Kit for viral RNA. 17 ul of RNA is added to the amplification master mix. The master mix contains (per reaction) 0.2 ul of SEQ ID No. 1 (30 pmole/ul), 0.4 ul of SEQ ID No. 7 (30 pmole/ul), 6.4 ul of water, 1.75 ul of dNTP, 1.165 ul of DTT, and 0.58 ul of Rnase inhibitor. The reactions are thermocycled using a Perkin-Elmer 9700 thermocycler using the following temperature/time cycle program:

|  |  |  | 20 cycles | | | 15 cycles | | | | |
|---|---|---|---|---|---|---|---|---|---|---|
| 90 C. | 50 C. | 94 C. | 94 C. | 57 C. | 72 C. | 94 C. | 60 C. | 70 C. | 70 C. | 4 C. |
| 2 | 60 | 2 | 30 | 30 | 1.5 | 30 | 30 | 2 | 7 | hold |

After incubating the amplification master mix and the RNA together for five minutes at 50 C, 4 ul of a second master mix is added and the RT-PCR cycle program is continued. The second master mix contains 10 ul of RT-PCR buffer, 5 ul of Rnase inhibitor, 1 ul of reverse transcriptase enzyme (Superscript, Invitrogen Corporation), and 17.5 ul of DNA polymerase. After the PCR cycle program was completed, samples were sequenced according to the protocol in the TRUGENE HIV-1 package insert (Visible Genetics Inc.).

The following samples were successfully amplified and sequenced. Viral load numbers are provided as copies of viral RNA per milliliter of patient plasma. "Origin" refers to the residence of the patient at the time the plasma was collected.

| Sample | ID | Subtype | ORIGIN | TYPE | Viral Load |
|---|---|---|---|---|---|
| 1 | I-001 | B | USA | co-culture | unknown |
| 2 | I-002 | A/G | USA | co-culture | unknown |
| 3 | I-003 | F | USA | co-culture | $7.5 \times 10^7$ |
| 4 | I-004 | B | USA | co-culture | Unknown |
| 5 | I-005 | Group O | USA | co-culture | Unknown |
| 6 | I-006 | E | USA | co-culture | $6.4 \times 10^6$ |
| 7 | I-007 | E | USA | co-culture | $2.6 \times 10^9$ |
| 8 | I-008 | B | USA | co-culture | Unknown |
| 9 | I-009 | E | USA | co-culture | $4.4 \times 10^5$ |
| 10 | I-010 | E | USA | co-culture | unknown |
| 11 | I-011 | E | USA | co-culture | $1.1 \times 10^7$ |
| 12 | I-012 | C | USA | co-culture | $6.9 \times 10^6$ |
| 13 | I-013 | B | USA | co-culture | Unknown |

-continued

| Sample | ID | Subtype | ORIGIN | TYPE | Viral Load |
|---|---|---|---|---|---|
| 14 | I-014 | F | USA | co-culture | Unknown |
| 15 | I-015 | F/B | USA | co-culture | $2.1 \times 10^6$ |
| 16 | I-016 | B | USA | co-culture | Unknown |
| 17 | I-017 | C | USA | co-culture | $5.6 \times 10^5$ |
| 18 | 1747 | A | NIH Repos. | co-culture | $2.5 \times 10^4$ |
| 19 | 2386 | D | NIH Repos. | co-culture | $4 \times 10^4$ |
| 20 | W1-1 | A | Europe | patient plasma | $2.1 \times 10^4$ |
| 21 | W1-2 | A | Europe | patient plasma | $1.4 \times 10^5$ |
| 22 | W1-3 | C | Europe | patient plasma | $2.1 \times 10^4$ |
| 23 | W1-4 | D | Europe | patient plasma | $6.2 \times 10^4$ |
| 24 | W1-5 | C | Europe | patient plasma | $9.4 \times 10^4$ |
| 25 | W1-6 | A | Europe | patient plasma | $8.5 \times 10^4$ |
| 26 | W1-7 | D | Europe | patient plasma | $5.6 \times 10^5$ |
| 27 | W1-8 | F | Europe | patient plasma | $5.7 \times 10^3$ |
| 28 | W1-9 | C | Europe | patient plasma | Unknown |
| 29 | W1-10 | G | Europe | patient plasma | Unknown |
| 30 | W1-11 | F | Europe | patient plasma | $1.6 \times 10^5$ |
| 31 | W1-12 | G | Europe | patient plasma | $5.6 \times 10^5$ |
| 32 | W1-13 | G | Europe | patient plasma | $2.3 \times 10^3$ |
| 33 | W2-1 | A | Europe | patient plasma | $2.2 \times 10^4$ |
| 34 | W2-2 | A | Europe | patient plasma | $1.4 \times 10^5$ |
| 35 | W2-3 | C | Europe | patient plasma | $2.1 \times 10^4$ |
| 36 | 13866 | B | Israel | patient plasma | $1.4 \times 10^4$ |
| 37 | 15089 | B | Israel | patient plasma | $1.0 \times 10^3$ |
| 38 | 15214 | A | Israel | patient plasma | $2.0 \times 10^3$ |
| 39 | 15422 | C | Israel | patient plasma | $1.1 \times 10^6$ |
| 40 | 16100 | C | Israel | patient plasma | $7.2 \times 10^5$ |
| 41 | 16242 | C | Israel | patient plasma | $7.2 \times 10^5$ |
| 42 | 16360 | C | Israel | patient plasma | $2.6 \times 10^5$ |
| 43 | 16361 | C | Israel | patient plasma | $2.2 \times 10^5$ |
| 44 | NA | A/G | Russia | patient plasma | $2.0 \times 10^5$ |
| 45 | NA | C | Africa | patient plasma | $6.3 \times 10^3$ |
| 46 | NA | B | Israel | patient plasma | $7.6 \times 10^4$ |
| 47 | NA | C | Ethiopia | patient plasma | $9.2 \times 10^4$ |
| 48 | NA | C | Ethiopia | patient plasma | $4.1 \times 10^5$ |
| 49 | NA | C | Ethiopia | patient plasma | $2.5 \times 10^4$ |
| 50 | NA | unknown | Argentina | patient plasma | $7.3 \times 10^3$ |
| 51 | NA | unknown | Argentina | patient plasma | $3.6 \times 10^4$ |
| 52 | NA | C | Ethiopia | patient plasma | $7.3 \times 10^4$ |
| 53 | NA | unknown | Argentina | patient plasma | $4.8 \times 10^5$ |
| 54 | NA | C | Ethiopia | patient plasma | $1.2 \times 10^5$ |
| 55 | NA | C | Ethiopia | patient plasma | $2.7 \times 10^5$ |
| 56 | NA | C | Ethiopia | patient plasma | $1.9 \times 10^5$ |
| 57 | NA | C | Ethiopia | patient plasma | $5.3 \times 10^4$ |
| 58 | NA | C | Ethiopia | patient plasma | $1.6 \times 10^4$ |
| 59 | NA | C | Ethiopia | patient plasma | $1.1 \times 10^5$ |
| 60 | NA | C | Ethiopia | patient plasma | $9.3 \times 10^4$ |
| 61 | NA | C | Ethiopia | patient plasma | $3.8 \times 10^4$ |
| 62 | NA | C | Ethiopia | patient plasma | $1.0 \times 10^3$ |
| 63 | NA | C | Ethiopia | patient plasma | $2.8 \times 10^4$ |
| 64 | NA | C | Ethiopia | patient plasma | $1.4 \times 10^4$ |
| 65 | NA | C | Ethiopia | patient plasma | $7.5 \times 10^5$ |
| 66 | NA | B | Israel | patient plasma | $5.5 \times 10^5$ |
| 67 | NA | unknown | Israel | patient plasma | $3.2 \times 10^4$ |
| 68 | NA | C | Ethiopia | patient plasma | unknown |
| 69 | NA | B | Europe | patient plasma | unknown |
| 70 | NA | K | Ivory Coast | patient plasma | unknown |

Example 2

Oligonucleotide primers in accordance with the present invention were tested to determine what percentage of non-B subtypes could be genotyped using samples that could not be genotyped using the TRUGENE HIV-1 genotyping kit. 74% of those samples were successfully genotyped. Similarly, greater than 95% of all samples known to be non-B samples were successfully genotyped using the oligonucleotide primers of the present invention. Panels of non-B subtype viruses were generated, using pLAI as a positive control. After a viral load for each sample was obtained (Roche Amplicor or Organon Teknika NASBA), samples were diluted, using a serial dilution procedure, down to 25 copies per reverse transcriptase reaction. In each case, successful base calling and mutation detection was achieved.

Example 3

Using the primers of the present invention, successful amplification and sequencing of HIV-1 viruses from both Group M (various subtypes and recombinants) and Group O was achieved.

| HIV-1 Type or Subtype | Number non-B's tested | Mean % Sucessfully Amplified |
|---|---|---|
| A (Group M) | n = >7 | >95% |
| B (Group M) | n = >200 | >95% |
| C (Group M) | n = >29 | >95% |
| D (Group M) | n = >3 | >95% |
| E (Group M) | n = >5 | >95% |
| F (Group M) | n = >25 | >95% |
| G (Group M) | n = 3 | >95% |
| K (Group M) | n = 1 | 100% |
| Group O | n = 2 | 100% |
| Group M Recombinants | n = 6 | 100% |

The invention claimed is:

1. A primer combination comprising, in a single solution, at least two species of forward HIV-1 sequencing primers selected from among primers comprising a sequence represented by the degenerate sequence RARRARGGGCTGYTGGARATGTS, (Seq ID No. 9)

or

GGAAAAAGGGCTGTTGGAAATGYG, (Seq. ID No.: 1)

and at least two species of reverse HIV-1 sequencing primers selected from among primers comprising a sequence represented by the degenerate sequence AGTCARATYTAYBCWGGGATYAARGTRADGV, (Seq. ID No.: 10)

GTCARATYTAYBCWGGGATYAARGTRADGV, (Seq. ID No.: 12)

GYCAGATTTACCCAGGGATTAAAGTAAGGC, or (Seq. ID No. 7)

AGYCAGATTTACCCAGGGATTAAAGTAAGGC, (Seq. ID No. 8)

wherein the forward and reverse sequencing primers are members of a set of degenerate forward and reverse primers.

2. The primer combination of claim 1, wherein at least one forward sequencing primer comprises a sequence selected from the group consisting of:

| GGAAAAAGGGCTGTTGGAAATGTGG, | (Seq. ID No.: 17) |
|---|---|
| GGAAAAAGGGCTGTTGGAAATGTG, | (Seq. ID No.: 18) |
| GGAAAAAGGGCTGTTGGAAATGTCG, | (Seq. ID No.: 19) |
| GGAAAAAGGGCTGTTGGAAATGTC, | (Seq. ID No.: 11) |
| GRARRARGGGCTGTTGGAAATGTGG, | (Seq. ID No.: 2) |
| GRARRARGGGCTGTTGGAAATGTG, | (Seq. ID No.: 3) |
| GAAAAAGGGCTGTTGGAAATGTG, and | (Seq. ID No.: 15) |
| GAAAAAGGGCTGTTGGAAATGCG. | (Seq. ID No.: 16) |

3. The primer combination of claim 1, wherein at least one reverse sequencing primer comprises a sequence selected from the group consisting of:

| AGTCAGATTTACCCAGGGATTAAAG-TAAGGV, | (Seq. ID No. 4) |
|---|---|
| AGTCAGATTTACCCAGGGATTAAGG-TAAGGV, | (Seq. ID No. 5) |
| AGTCAGATTTACCCAGGGATCAAAG-TAAGGV, | (Seq. ID No. 6) |
| GTCAGATTTACCCAGGGATTAAAGTAAGGC, and | (Seq. ID No.: 13) |
| GCCAGATTTACCCAGGGATTAAAGTAAGGC. | (Seq. ID No.: 14) |

4. The primer combination of claim 3, wherein at least one forward sequencing primer comprises a sequence selected from the group consisting of:

| GGAAAAAGGGCTGTTGGAAATGTGG, | (Seq. ID No.: 17) |
|---|---|
| GGAAAAAGGGCTGTTGGAAATGTG, | (Seq. ID No.: 18) |
| GGAAAAAGGGCTGTTGGAAATGTCG, | (Seq. ID No.: 19) |
| GGAAAAAGGGCTGTTGGAAATGTC, | (Seq. ID No.: 11) |
| GRARRARGGGCTGTTGGAAATGTGG, | (Seq. ID No.: 2) |
| GRARRARGGGCTGTTGGAAATGTG, | (Seq. ID No.: 3) |
| GAAAAAGGGCTGTTGGAAATGTG, and | (Seq. ID No.: 15) |
| GAAAAAGGGCTGTTGGAAATGCG. | (Seq. ID No.: 16) |

5. The primer combination of claim 1, wherein the forward sequencing primers are members of the set of degenerate primers comprising the sequence: GGAAAAAGGGCTGTTGGAAATGYG (Seq. ID No.: 1).

6. The primer combination of claim 5, wherein the reverse sequencing primers are members of the set of degenerate primers comprising the sequence: GYCAGATTTACCCAGGGATTAAAGTAAGGC (Seq. ID No. 7).

7. The primer combination of claim 6, wherein the reverse primers have the sequence as set forth in Seq. ID Nos. 13 and 14.

8. The primer combination of claim 1, wherein the reverse sequencing primers are members of the set of degenerate primers comprising the sequence: GYCAGATTTAC-CCAGGGATTAAAGTAAGGC (Seq. ID No. 7).

9. The primer combination of claim 1, wherein the forward sequencing primers or the reverse sequencing primers are labeled with a detectable label.

10. The primer combination of claim 9, wherein the detectable label is a fluorescent label.

11. A genotyping kit comprising at least two species of forward HIV-1 sequencing primers selected from among primers comprising a sequence represented by the degenerate sequence

```
                                         (Seq ID No. 9)
RARRARGGGCTGYTGGARATGTS, or (Seq. ID No.: 1)
GGAAAAAGGGCTGTTGGAAATGYG,
``` and at least two species of reverse HIV-1 sequencing primers selected from among primers comprising a sequence represented by the degenerate sequence

```
                                         (Seq. ID No.: 10)
AGTCARATYTAYBCWGGGATYAARGTRADGV, (Seq. ID No. 12)
GTCARATYTAYBCWGGGATYAARGTRADGV, (Seq. ID No. 7)
GYCAGATTTACCCAGGGATTAAAGTAAGGC, or (Seq. ID No. 8)
AGYCAGATTTACCCAGGGATTAAAGTAAGGC,
``` wherein the forward and reverse sequencing primers are members of a set of degenerate forward and reverse primers.

12. The kit of claim 11, wherein at least one forward sequencing primer is selected from the group consisting of:

```
GGAAAAAGGGCTGTTGGAAATGTGG,      (Seq. ID No.: 17)

GGAAAAAGGGCTGTTGGAAATGTG,       (Seq. ID No.: 18)

GGAAAAAGGGCTGTTGGAAATGTCG,      (Seq. ID No.: 19)

GGAAAAAGGGCTGTTGGAAATGTC,       (Seq. ID No.: 11)

GRARRARGGGCTGTTGGAAATGTGG,      (Seq. ID No.: 2)

GRARRARGGGCTGTTGGAAATGTG,       (Seq. ID No.: 3)

GAAAAAGGGCTGTTGGAAATGTG,        (Seq. ID No.: 15)
and

GAAAAAGGGCTGTTGGAAATGCG.        (Seq. ID No.: 16)
```

13. The kit of claim 11, wherein at least one reverse sequencing primer is selected from the group consisting of:

```
                                         (Seq. ID No. 4)
AGTCAGATTTACCCAGGGATTAAAGTAAGGV, (Seq. ID No. 5)
AGTCAGATTTACCCAGGGATTAAGGTAAGGV, (Seq. ID No. 6)
AGTCAGATTTACCCAGGGATCAAAGTAAGGV,
```

```
                                         (Seq. ID No.: 13)
GTCAGATTTACCCAGGGATTAAAGTAAGGC, and (Seq. ID No.: 14)
GCCAGATTTACCCAGGGATTAAAGTAAGGC.
```

14. The kit of claim 13, wherein at least one forward sequencing primer is selected from the group consisting of:

```
                                         (Seq. ID No.: 17)
GGAAAAAGGGCTGTTGGAAATGTGG, (Seq. ID No.: 18)
GGAAAAAGGGCTGTTGGAAATGTG, (Seq. ID No.: 19)
GGAAAAAGGGCTGTTGGAAATGTCG, (Seq. ID No.: 11)
GGAAAAAGGGCTGTTGGAAATGTC, (Seq. ID No.: 2)
GRARRARGGGCTGTTGGAAATGTGG, (Seq. ID No.: 3)
GRARRARGGGCTGTTGGAAATGTG, (Seq. ID No.: 15)
GAAAAAGGGCTGTTGGAAATGTG, and (Seq. ID No.: 16)
GAAAAAGGGCTGTTGGAAATGCG.
```

15. The kit of claim 11, wherein the forward sequencing primers are members of the set of degenerate primers comprising the sequence:

```
GGAAAAAGGGCTGTTGGAAATGYG.       (Seq. ID No.: 1)
```

16. The kit of claim 15, wherein the reverse sequencing primers are members of the set of degenerate primers comprising the sequence:

```
GYCAGATTTACCCAGGGATTAAAGTAAGGC.  (Seq. ID No. 7)
```

17. The kit of claim 16, wherein the reverse primers have the sequences as set forth in Seq. ID Nos. 13 and 14.

18. The kit of claim 11, wherein the reverse sequencing primers are members of the set of degenerate primers comprising the sequence:

```
GYCAGATTTACCCAGGGATTAAAGTAAGGC.  (Seq. ID No. 7)
```

19. The kit of claim 11, wherein the forward sequencing primers or the reverse sequencing primers are labeled with a detectable label.

20. The kit of claim 19, wherein the detectable label is a fluorescent label.

21. The kit of claim 11, wherein the kit further comprises one or more reagents selected from the group consisting of an RNase inhibitor, a reverse transcriptase, a polymerase, and dNTP and ddNTP feedstocks.

22. The kit of claim 21, wherein the forward sequencing primers or the reverse sequencing primers are labeled with a detectable label.

23. The kit of claim 22, wherein the detectable label is a fluorescent label.

24. A method for evaluating a sample suspected of containing a non-B Group M HIV-1 virus or a Group O HIV-1 virus to assess the type of the virus, comprising the steps of:
   treating the sample to recover viral RNA;
   reverse transcribing the recovered viral RNA;
   sequencing the reverse transcription product;
   and using the results of the sequencing step to establish the genotype of the tested virus, wherein at least one of the reverse transcription step and the sequencing step is performed using the primer combination of claim 1.

25. The method of claim 24, further comprising the step of performing parallel genotyping procedures that are designed to evaluate B-subtype HIV-1 virus.

26. The method of claim 24, wherein the sample is one that has previously been the subject of a failed genotyping attempt using genotyping procedures that are designed to evaluate B-subtype virus.

* * * * *